United States Patent
Fletcher et al.

(10) Patent No.: US 10,777,298 B2
(45) Date of Patent: Sep. 15, 2020

(54) ANALYZING IMMUNE SIGNALING NETWORKS FOR IDENTIFICATION OF THERAPEUTIC TARGETS IN COMPLEX CHRONIC MEDICAL DISORDERS

(71) Applicants: NOVA SOUTHEASTERN UNIVERSITY, Fort Lauderdale, FL (US); UNIVERSITY OF MIAMI, Miami, FL (US); UNIVERSITY OF ALBERTA, TEC EDMONTON, Edmonton, Alberta, CA (US)

(72) Inventors: Mary Ann Fletcher, Miami, FL (US); Gordon Broderick, Edmonton, Alberta, CA (US); Nancy Klimas, Fort Lauderdale, FL (US); Zachary Barnes, Miami, FL (US)

(73) Assignees: Nova Southeastern University, Fort Lauderdale, FL (US); University of Miami, Miami, FL (US); University of Alberta, TEC Edmonton, Edmonton, CA (US)

( * ) Notice: Subject to any disclaimer, the term of this patent is extended or adjusted under 35 U.S.C. 154(b) by 762 days.

(21) Appl. No.: 15/028,757

(22) PCT Filed: Oct. 14, 2014

(86) PCT No.: PCT/US2014/060535
§ 371 (c)(1),
(2) Date: Apr. 12, 2016

(87) PCT Pub. No.: WO2015/054701
PCT Pub. Date: Apr. 16, 2015

(65) Prior Publication Data
US 2016/0275236 A1   Sep. 22, 2016

Related U.S. Application Data

(60) Provisional application No. 61/890,297, filed on Oct. 13, 2013.

(51) Int. Cl.
G16B 5/00 (2019.01)
G16B 40/00 (2019.01)
A61K 38/20 (2006.01)

(52) U.S. Cl.
CPC ............ *G16B 5/00* (2019.02); *A61K 38/2086* (2013.01); *G16B 40/00* (2019.02)

(58) Field of Classification Search
None
See application file for complete search history.

(56) References Cited

U.S. PATENT DOCUMENTS 6,258,352 B1   7/2001   Shimonaka
6,309,668 B1  10/2001   Bastin
(Continued)

FOREIGN PATENT DOCUMENTS

WO        2015054701        10/2014

OTHER PUBLICATIONS

Broderick et al., (Brain Behav Immun. 2011.25(2):302-13. ePub Oct. 15, 2010), (Year: 2010).*
(Continued)

*Primary Examiner* — Olivia M. Wise
(74) *Attorney, Agent, or Firm* — Fleit Intellectual Property Law; Paul D. Bianco; Katherine Wong Davis (57) ABSTRACT

A general method of analyzing immune signaling networks for identification of potential therapeutic targets in complex, chronic medical disorders is described. The disclosure provides the CD3−/CD56+ natural killer (NK) cell population as a potential therapeutic target in the clinically-overlapping disorders Gulf War Illness (GWI) and Myalg Encephalomyelitis/Chronic Fatigue Syndrome (ME/CFS). The disclosure also provides a method for improving or restoring Natural Killer (NK) cell function by stimulating the NK cells with interleukin-15 (IL-15).

15 Claims, 5 Drawing Sheets

(56) References Cited

U.S. PATENT DOCUMENTS

| | | |
|---|---|---|
| 6,521,431 B1 | 2/2003 | Kiser |
| 2012/0244118 A1 | 9/2012 | Berraondo |

OTHER PUBLICATIONS

LaManca et al. Immunological Response in Chronic Fatigue Syndrome Following a Graded Exercise Test to Exhaustion. Journal of Clinical Immunology, vol. 19, No. 2, pp. 135-142 (Year: 1999).*
Broderick et al. Supplementary Data of Altered immune pathway activity under exercise challenge in Gulf War Illness: An exploratory analysis. Brain, Behavior, and Immunity, vol. 28, pp. 159-169 (Year: 2013).*
2 Fukuda K. et al. Chronic Multi-symptom Illness Affecting Airforce Veterans of the Gulf War, JAMA 280:981-998; Sep. 16, 1998.
3 Wolfe J. et al. . Health Symptoms Reported by Persian Gulf War Veterans two year after return, Am J. Ind. Med. 33(2):104-113; 1998.
4 Kang H, et al., Post Traumatic Stress Disorder and Chronic Fatigue Syndrome-like Illness among Gulf War Veterans, Am J Epidemiol 157:141-148; 2003.
6 Golier J. et al. ,Enhanced Cortisol Suppression to Dexamethasone Associated with Gulf War Deployment, Psychoneuroendocrinology 31(10):1181-1189; 2006.
7 Golier J. et al. Twenty-four Hour Plasma Cortisol and Adrenocorticotropic Hormone in Gulf War Veterans, Biol Psychiatry 62(10):1175-1178; Apr. 2007.
8 Unwin C. et al. Health of UK Servicemen Who Served in Persian Gulf War, Lancet 353:169-178; Jan. 16, 1999.
9 Crofford L. et al. Basal Circadian and Pulsatile ACTH and Cortisol Secretion Inpatients with Fibromyalgia and/or Chronic Fatigue Stndrome, Brain Behav Immun; 18:314-325; 2004.
10 Johnson J. et al.The Role of IL-1beta in Stress Induced Sensitization of Pro-inflammatory Cytokine and Corticosterone Responses. Neuroscience 127(3):569-577; 2004.
11 Morgan C. et al., Neuropeptide-Y, Cortisol, and Subjective Distress in Humans Exposed to Acute Stress: Replication and Extension of Previous Report. Biol Psychiatry 52(2):136-142; 2002.
12 Butts C. et al. Neuroendocrine Factors Alter Host Defense by Modulating Immune Function. Cell Immunol 252(1-2):7-15; 2008.
13 Medical Dictionary for the Health Professions and Nursing © Farlex 2012, obtained from the Free Dictionary website on Oct. 10, 2014.
14 Feriazzo G. et al., Distinct roles of IL-12 and IL-15 in Human Natural Killer Cell Activation by Dendritic Cells from Secondary Lymphoid Organs; PNAS 101(47):16606-16611; Nov. 23, 2004.
15 Broderick G. et al., Brain Behavior and Immunity; A Pilot Study of Immune Ntework Remodeling under Challenge in Gulf War Illness; Elsevier; vol. 25:302-313; Feb. 2011.
16 Broderick G. et al., Brain Behavior and Immunity; Altered Immune Pathway Activity under Exercise Challenge in Gulf War Illness; Elsevier; vol. 28:159-169; Feb. 2013.
17 Collins J. et al., Controlled Clinical Trials; The Antibiotic Treatment Trial of Gulf War Veterans Illnesses; 23 (3):333-353; 2002.
19 Fletcher M. et al., Methods Molecular Biology, Psychoneuroimmunology and Natural Killer Cells; 934:313-324; 2012.
20 Ranson T. et al., IL-15 is an Essential Mediator of Peripheral NK-Cell Homeostasis; 101(12);4887-4893; Jun. 2003.
21 Fletcher, M. et al., Journal of Translational Medicine; Plasma Cytokines in Women with Chronic Fatigue Syndrome; 7:96, pp. 1-8, Nov. 2009.
Broderick et al., A Pilot Study of Immune Network Remodeling under Challenge in Gulf War Illness, Brian Behav Immun 2011—PubMed, dated Feb. 2011.
Broderick et al., Altered Immune Pathway under Exercise Challenge in Gulf War Illness: an exploratory analysis, Brian Behav Immun 2013—PubMed dated Feb. 2013.
Cheng, Expert Opinion, Analysing Microarray data in drug discovery using system biology, 02(5) 755-68; p. 756, col. 2; 759,Fig 2 and its legend; p. 761, col. 2, 2007.
Sean C. Bendall et al.,Single-Cell mass Cytometry of Differential Immune and Drug Responses Across a Human Hematopoietic Continuum, Science, vol. 332, May 6, 2011.
Ekua W. Brenu et al., Immunological Abnormalities as Potential Biomarker in Chronic Fatigue Syndrome/Myalgic Encephalomyelitis; BioMed Central, Journal of Translational Medicine, 2011.
Broderick et al., A Pilot Study of Immune Network Remodeling under Challenge in Gulf War Illness, Brian Behav Immun 2011—PubMed, dated Feb. 2011, Abstract.
Broderick et al., Altered Immune Pathway under Exercise Challenge in Gulf War Illness: an Exploratory Analysis, Brian Behav Immun 2013—PubMed dated Feb. 2013, Abstract.
Travis J.A. Craddock et al., A Role for Homeostatic Drive in the Perpetuation of Complex Chronic Illness: Gulf War Illness and Chronic Fatigue Syndrome, PLOS One, vol. 9, issue 1, Jan. 2017.
Guido Feriazzo et al., Distinct roles of IL-12 and IL-15 in Human Natural Killer Cell Activation by Dendritic Cells from Secondary lymphoid Organs, 16606-16611—PNAS, vol. 101, No. 47, Nov. 23, 2004.
Mary Ann Fletcher et al., Plasma Cytokines in Women with Chronic Fatigue Syndrome, BioMed Central, Journal of Translational Medicine, Nov. 12, 2009.
http://medical-dictionary.thefreedictionary.com—the definition of graded exercise text by medical dictionary dated Oct. 10, 2014.
Thomas Ranson et al., IL-15 is an Essential Mediator of Peripheral NK Cell Homeostasis, Immunobiology, Blood, vol. 101, No. 12, Jun. 15, 2003.
Anne Liese Smylie et al.,A Comparison of Sex-Specific Immune Signatures in Gulf War Illness and Chronic Fatigue Syndrome, BioMed Central Immunology,14:29, 2013.
International Search Report and Written Opinion dated Mar. 27, 2015 for PCT/US14/60535 filed Oct. 14, 2014.
Search Report for EP 14852430.9 dated May 17, 2017, 13 pages.
Haley R.W. Is Gulf War Syndrome due to Stress? Am J Epidemiol 146(9):695-703; Jan. 15, 1997.
Anne Liese Smylie et al., A Pilot Study of Sex-Specific Immune Signature in Gulf War Illness and Chronic Fatigue Syndrome, BMC Immunology, Biomed Central, vol. 14, No. 1, Jun. 25, 2013, 14 pages.

* cited by examiner

ANALYZING IMMUNE SIGNALING NETWORKS FOR IDENTIFICATION OF THERAPEUTIC TARGETS IN COMPLEX CHRONIC MEDICAL DISORDERS

CROSS REFERENCE TO RELATED APPLICATION

This application claims the benefit of U.S. Patent Application No. 61/890,297, filed 13 Oct. 2013 (entitled: DYSREGULATION OF CYTOKINES IN GULF WAR ILLNESS AND MYALGIC ENCEPHALOMYELITIS/CHRONIC FATIGUE SYNDROME (ME/CFS)), the contents of which are incorporated herein by reference in its entirety.

This invention was made with government support under AI065723 awarded by the National Institutes of Health. The government has certain rights in the invention.

FIELD OF THE DISCLOSURE

The disclosure generally relates to methods of analyzing immune signaling networks for identification of potential therapeutic targets in complex, chronic medical disorders, particularly to the application of these methods for identification of the CD3−/CD56+ natural killer (NK) cell population as a potential therapeutic target in the clinically-overlapping disorders Gulf War Illness (GWI) and Myalgic Encephalomyelitis/Chronic Fatigue Syndrome (ME/CFS), and most particularly to the therapeutic application of interleukin-15 (IL-15) for modulation of Natural Killer (NK) cell function in patients having Gulf War Illness (GWI) and Myalgic Encephalomyelitis/Chronic Fatigue Syndrome (ME/CFS).

BACKGROUND

Most diseases do not result from a single etiology, but rather from multiple interacting events involving numerous bodily systems and producing a constellation of symptoms and chronic impairment for the suffering patients. One such complex, chronic medical disorder has manifested in veterans of armed conflict in the Middle East during the 1990's.

An alarming number of Gulf War veterans returning from Operation Desert Storm have been afflicted with a complex constellation of symptoms including debilitating fatigue, musculoskeletal discomfort, skin rashes, and cognitive dysfunction (Haley R. W. *Am J Epidemiol* 146(9):695-703 1997; Fukuda K. et al. *JAMA* 280:981-998 1998; Wolfe J. et al. *Am J Ind Med* 33(2):104-113 1998). There is still no clear understanding of Gulf War Syndrome (GWS), also called Gulf War Illness (GWI), although evidence is mounting of immunological dysfunction in this population that may be potentiated by response to stress whether physiological, psychological, chemical, or other. Indeed clinical presentation of GWI overlaps strongly with that of another stress-mediated complex, chronic medical disorder: Myalgic Encephalomyelitis/Chronic Fatigue Syndrome (ME/CFS), also called Chronic Fatigue Syndrome/Myalgic Encephalomyelitis (CFS/ME) (Kang H. et al. *Am J Epidemiol* 157: 141-148 2003; Elsen S. et al. *Ann Int Med* 142:881-890 2005). Dysregulation of the hypothalamic-pituitary-adrenal (HPA) axis has been linked to the pathophysiology of both GWI (Golier J. et al. *Psychoneuroendocrinology* 31(10): 1181-1189 2006; Golier J. et al. *Biol Psychiatry* 62(10): 1175-1178 2007; Unwin C. et al. *Lancet* 353:169-178 1999) and ME/CFS (Crofford L. et al. *Brain Behav Immun* 18:314-325 2004). Associated pathophysiology includes hypersensitivity of normal cytokine feedback to the HPA axis (Johnson J. et al. *Neuroscience* 127(3):569-577 2004) as well as the expected stress-induced release of neuropeptides such as neuropeptide-Y (NPY) and its mediation of innate immune response and cortisol levels (Morgan C. et al. *Biol Psychiatry* 52(2):136-142 2002).

Changes within the immune signaling network have also been observed in GWI and ME/CFS. There is a growing body of evidence supporting a significant role for factors produced by the nervous and endocrine systems in altering immune cell function (Butts C. et al. *Cell Immunol* 252(1-2):7-15 2008).

Without being bound by theory, it is proposed that complex, chronic medical disorders such as GWI and ME/CFS present with distinct patterns of immune signaling which will be different from the healthy, normal patterns. Considering the extensive amount of debilitating symptoms experienced by persons suffering from these conditions, it would be very advantageous to develop methods for analyzing and comparing these immune signaling patterns for identification of potential therapeutic targets and development of improved treatment strategies.

SUMMARY OF THE DISCLOSURE

A general method of analyzing immune signaling networks for identification of potential therapeutic targets in complex, chronic medical disorders is described herein. By carrying out the general method, the disclosure provides the CD3−/CD56+ natural killer (NK) cell population as a potential therapeutic target in the clinically-overlapping disorders Gulf War Illness (GWI) and Myalgic Encephalomyelitis/Chronic Fatigue Syndrome (ME/CFS). The disclosure also provides a method for improving or restoring Natural Killer (NK) cell function by stimulating the NK cells with interleukin-15 (IL-15) as a potential improved treatment strategy for GWI and ME/CFS.

In one aspect, the disclosure provides a method of analyzing immune signaling networks for identification of potential therapeutic targets in complex, chronic medical disorders. The method includes the steps of: selecting a group of subjects having a complex, chronic medical disorder as an experimental group; selecting a group of healthy subjects not having the complex, chronic medical disorder as a control group; subjecting both the experimental group and the control group to test conditions to induce expression of an immune signaling network in the subjects of both the experimental group and the control group; collecting blood samples from each subject tested at a predetermined number of time points before, during, and after subjecting the subjects to the test conditions; analyzing the blood samples to identify immune cell populations (a non-limiting example of immune cells are lymphocytes) and abundance in each sample; applying a computational approach using dynamic modeling to infer a directed immune response network describing coordinated dynamics of the immune cell populations identified and identifying a single consensus immune signaling network for the experimental group and a single consensus immune signaling network for the control group; and analyzing and comparing the consensus immune signaling networks for changes in structure and information flow to identify potential therapeutic targets for the complex, chronic medical disorder.

This method can be used to identify therapeutic targets for improved treatment strategies in any disorder. Preferred, non-limiting examples are complex, chronic medical disorders such as Gulf War Illness (GWI) and Myalgic Encephalomyelitis/Chronic Fatigue Syndrome (ME/CFS).

A non-limiting example of test conditions used in the method is a graded exercise test (GXT) for subjecting the subjects of both groups to an exercise challenge to induce expression of an immune signaling network in response to exercise in the subjects. A graded exercise test is multistage exercise testing (usually on a treadmill or bicycle ergometer) in which exercise intensity is progressively increased (graded) through levels that bring the test subject to a self-imposed fatigue level (Medical Dictionary for the Health Professions and Nursing ©Farlex 2012, obtained from the Free Dictionary website on Oct. 10, 2014).

In the method, blood samples are collected at nine time points across the exercise challenge during a time period of twenty four hours; baseline, baseline plus 3 minutes, VO2 max (maximum effort), 10 minutes, 20 minutes, 30 minutes, 60 minutes, and 4 hours after VO2 max, and next day.

The blood samples are preferably, but not exclusively analyzed using flow cytometry. In flow cytometry, immune cell populations can be identified by staining for the presence/absence of specific cell surface markers, usually called cluster designation or CD markers. In the experiments described herein, 12 lymphocyte populations are identified; CD19+, CD3+CD4+, CD3+CD8+, CD3+, CD3−/CD56+, CD3−/CD16+, CD2+, CD2+CD26+, CD4+CD26+, CD8+CD26+, CD8+CD11a+, and CD3−/CD16+CD11a+.

In the described method, applying a computational approach can include using dynamic modeling such as applying a linear rate equation model and a projection-based parameter estimation technique. In one aspect, dynamic modeling uses complex data sets including at least one of immune function, quantification of immune peptides, quantification of neuropeptides, and genomic studies to determine patterns useful in refining biomarker panels.

Additionally, in the described method analyzing and comparing the consensus immune signaling networks for changes in structure and information flow includes applying a graph theoretical analysis.

Therapeutic targets identified by carrying out the described method can be, but are not limited to, markers of nervous, endocrine, or immune regulation. Non-limiting examples of markers are peptides, proteins, nucleic acids, small biological molecules, biomarkers, cytokines, chemicals, chemical compounds, and interleukins. A particularly preferred marker is a cytokine marker of immune regulation. A preferred, non-limiting example of such a cytokine marker of immune regulation is interleukin 15 (IL-15).

Therapeutic targets identified by carrying out the described method can also be, but are not limited to specific immune cell populations. A particularly preferred, non-limiting example of such an immune cell population is a CD3−/CD56+ natural killer (NK) cell population.

In another aspect, the disclosure provides a pharmaceutical composition comprising a therapeutically-effective amount of an exogenous interleukin-15 (IL-15) and a pharmaceutically-acceptable carrier.

In yet another aspect, the disclosure provides a method for improving or restoring Natural Killer (NK) cell function in a subject having impaired NK cell function. This method can include the steps of, but is not limited to, providing a composition including a therapeutically-effective amount of an exogenous interleukin-15 (IL-15) and a pharmaceutically-acceptable carrier; and administering the composition to the subject to stimulate the NK cells such that function is restored or improved.

As used herein, the term "subject" can refer to a human patient or to an animal patient.

Impaired NK cell function, i.e. loss of cytotoxic activity, is often found in patients having a complex, chronic medical condition including dysregulation of cytokines. Dysregulation of cytokines can be manifested by low levels of interleukin-15 (IL-15) as it is in Gulf War Illness (GWI) and Myalgic Encephalomyelitis/Chronic Fatigue Syndrome (ME/CFS).

As used herein, the term "natural killer (NK) cells" refer to both NK cells of the peripheral blood and the NK cells of lymphoid organs (Feriazzo G. et al. *PNAS* 101(47):16606-16611 2004).

Figure 2:
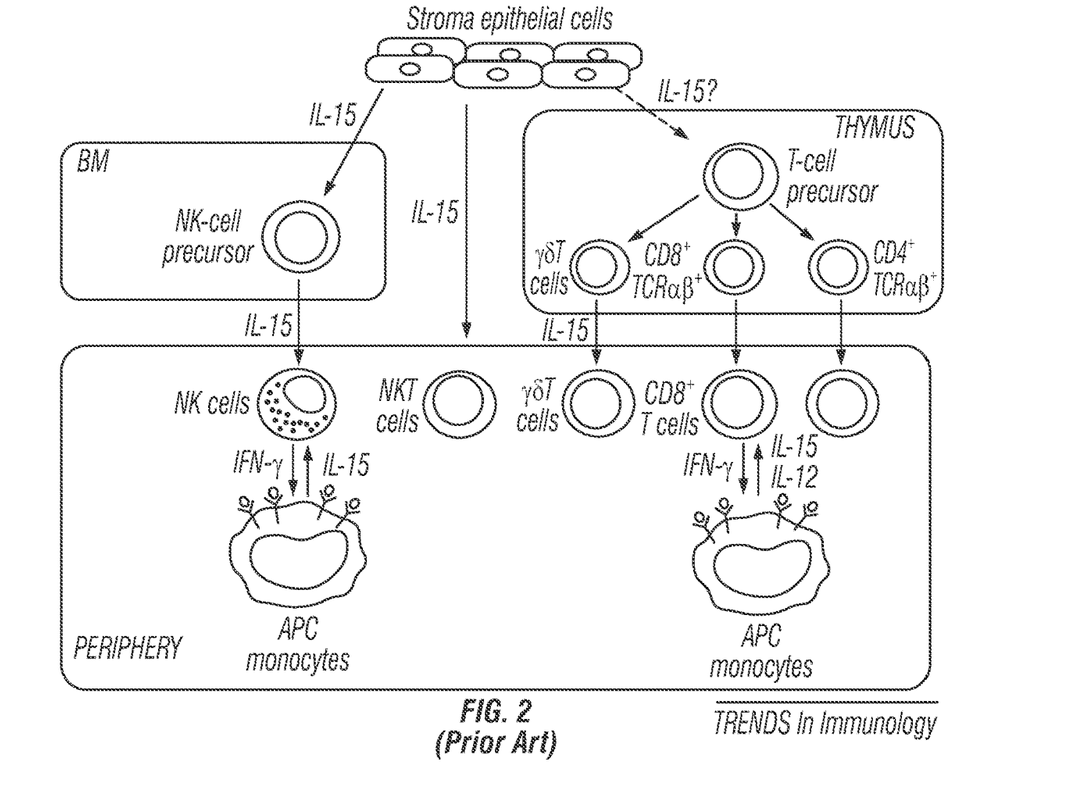
FIG. 2 is a schematic drawing obtained from TRENDS in Immunology illustrating the function of interleukin-15 (IL-15).

As used herein, the phrase "improving or restoring Natural Killer (NK) cell function" refers to improving or restoring the cytotoxic activity of NK cells. Stimulation of the NK cells by interleukin 15 (IL-15) can occur via pathways illustrated in FIG. 2. This schematic illustration was obtained from the journal *Trends in Immunology*.

As used herein, the term "exogenous interleukin 15 (IL-15)" refers to IL-15 that is derived externally from the subject or from the subject's cells.

The phrase "effective amount" refers to the amount of a composition necessary to achieve the composition's intended function.

The phase "therapeutically-effective amount" refers to the amount of a composition required to achieve the desired function, i.e. improvement and/or restoration of natural killer (NK) cell function. In the experiments described herein, the therapeutically-effective amount of exogenous interleukin 15 (IL-15) is at least about 25 ng/ml and the NK cell function is improved at least about three-fold from function at administration of the composition The phrase "pharmaceutically-acceptable carrier" refers to an inactive and non-toxic substance used in association with an active substance, i.e. exogenous interleukin 15 (IL-15), especially for aiding in the application of the active substance. Non-limiting examples of pharmaceutically-acceptable carriers are diluents, binders, disintegrants, flavorings, fillers, and lubricants. Pharmaceutically-acceptable carriers can have more than one function, i.e. a filler can also be a disintegrant. Additionally, pharmaceutically-acceptable carriers may also be referred to as non-medicinal ingredients (NMIs).

As used herein, the term "exogenous interleukin 15 (IL-15)" refers to IL-15 that is derived externally from the subject or from the subject's cells.

In an additional aspect of the disclosure, the herein described exogenous interleukin 15 (IL-15) and pharmaceutically-acceptable carriers can be used in the manufacture of any of the above-disclosed compositions and pharmaceutical compositions and used in any of the herein described methods.

Other objectives and advantages of this disclosure will become apparent from the following description taken in conjunction with the accompanying drawings, wherein are set forth, by way of illustration and example, certain embodiments of this disclosure. The drawings constitute a part of this specification and include exemplary embodiments of the present disclosure and illustrate various objects and features thereof.

BRIEF DESCRIPTION OF THE DRAWINGS

A more complete understanding of the present disclosure may be obtained by references to the accompanying drawings when considered in conjunction with the subsequent detailed description. The embodiments illustrated in the drawings are intended only to exemplify the disclosure and should not be construed as limiting the disclosure to the illustrated embodiments.

FIG. 3A is a chart graphing "betweeness in centrality" of the lymphocyte populations analyzed having cluster designation (CD) surface markers CD19+, CD3+CD4+, CD3+CD8+, CD3+, CD3−/CD56+, CD3−/CD16+, CD2+, CD2+CD26+, CD4+CD26+, CD8+ CD26+, CD8+CD11a+, and CD3−/CD16+CD11a+. The "betweeness centrality" of a network node is a measure of the amount of information throughput. In GWI, the NK cell CD3−/CD56+ fraction was the only cell type to lose in betweeness centrality. Healthy Control Numbers (HC #) are the bars in front and Gulf War Illness Numbers (GWI #) are the bars in the back. FIG. 3B shows empirical networks inferring directed interactions between 12 lymphocyte subpopulations (cell subpopulations shown in FIG. 3A) based on flow cytometry of whole blood samples collected at 9 points in time across an exercise challenge (baseline, baseline plus 3 minutes, VO2 max (maximum effort), 10 minutes, 20 minutes, 30 minutes, 60 minutes, and 4 hours after VO2 max, and next day) in healthy (n=18) and GWI (n=23) subjects. Arrowheads indicate a stimulatory contribution and t-bar connections indicate an inhibitory action.

DETAILED DESCRIPTION OF THE DISCLOSURE

For the purpose of promoting an understanding of the principles of the disclosure, reference will now be made to embodiments illustrated herein and specific language will be used to describe the same. It will nevertheless be understood that no limitation of the scope of the disclosure is thereby intended. Any alterations and further modification in the described compositions, formulations, and methods and any further application of the principles of the disclosure as described herein, are contemplated as would normally occur to one skilled in the art to which the disclosure relates.

Lymphocyte Population Dynamics in Gulf War Illness During Exercise Challenge: A Network Analysis Within months of returning from Operation Desert Storm an alarming number of veterans began a constellation of symptoms that would eventually be termed "Gulf War Illness (GWI)." This complex disorder affecting nervous, endocrine, and immune regulation may be mediated by the basic response to stressors whether physiological, psychological, chemical, or other. In view of this evidence, it is suspected that the structure of the immune signaling network normally expressed in humans in response to exercise will be significantly altered in GWI subjects.

It has been recently demonstrated that undirected immune signaling networks were altered in Gulf War veterans in response to an exercise challenge (Broderick G. et al. Brain Behav Immun 25:302-313 2011; Broderick G. et al. Brain Behav Immun 28:159-169 2013). Though undirected networks offer a powerful new fingerprint, additional information is required to simulate the flow of information throughout the network. Thus, the analysis has been extended to 9 time points in the experiments described herein using a linear rate equation model in order to get: a) direction, b) polarity (promote or inhibit), and c) the rate at which information is transmitted (kinetics).

The objectives of the experiments were to determine if the signal processing patterns between immune cell populations and sub-populations in GWI differ from healthy controls under exercise challenge and to determine which immune cell populations and sub-populations are most affected.

To explore this concept, interaction patterns linking immune markers and their evolution during exercise were compared. Blood samples were collected at 9 time points spanning 24 hours across a maximum $VO_2$ Graded Exercise Test (GXT) from n=23 GWI subjects and n=18 healthy controls. The subjects were recruited from Miami Veterans Administration Medical Center. Use of the Fukuda definition in GWI is supported by Collins J. et al. Control Clin Trials 23 (3):333-353 2002. The healthy control subjects were Gulf War era sedentary veterans and were matched to the GWI subjects by age, body mass index (BMI), and ethnicity.

A graded exercise test is multistage exercise testing (usually on a treadmill or bicycle ergometer) in which exercise intensity is progressively increased (graded) through levels that bring the test subject to a self-imposed fatigue level (Medical Dictionary for the Health Professions and Nursing ©Farlex 2012, obtained from the Free Dictionary website on Oct. 10, 2014).

In the described experiments, a standard graded eXercise test (McArdle W. et al. Exercise Physiology: Energy, Nutri-

*tion, and Human Performance*. London: Lippincott Williams & Wilkins 2007) was administered using a Vmax Spectra 29c Cardiopulmonary Exercise Testing Instrument, Sensor-Medics Ergoline 800 fully automated cycle ergometer, and Sensor-Medics Marquette Max 1 Stress ECG.

In the method, blood samples are collected at nine time points across the exercise challenge during a time period of twenty four hours; baseline, baseline plus 3 minutes, VO2 max (maximum effort), 10 minutes, 20 minutes, 30 minutes, 60 minutes, and 4 hours after VO2 max, and next day.

The blood samples were analyzed using flow cytometry. In flow cytometry, immune cell populations can be identified by staining for the presence/absence of specific cell surface markers, usually called cluster designation or CD markers. Flow cytometry was performed on each blood sample to determine lymphocyte subset abundance using a Beckman/Coulter FC500 flow cytometer. The abundance of 12 lymphocyte subsets were stained with appropriate antigens and the coloring scheme was determined by the Beckman/Coulter FC500 flow cytometer at the nine time points Immune cell populations were surface stained for CD19, CD2, CD3, CD4, CD8, CD26, CD56, CD16, and CD11a. Using a linear rate equation model, a projection-based parameter estimation technique was applied to each time course to infer a directed immune response network describing the coordinated dynamics of twelve lymphocyte subpopulations identified by cell surface markings (CD19+, CD3+CD4+, CD3+CD8+, CD3+, CD3−/CD56+, CD3−/CD16+, CD2+, CD2+CD26+, CD4+CD26+, CD8+CD26+, CD8+CD11a+, and CD3−/CD16+CD11a+).

Reverse Engineering: A linear rate equation model and a projection-based parameter estimation technique was applied to each time course to infer a directed immune response network describing the coordinated dynamics of the 12 lymphocyte subpopulations.

Model: $\frac{\partial x_i}{\partial t} = a_{i,1}x_1 + a_{i,2}x_2 + \ldots + a_{i,n}x_n$ Where $x_1, x_2, \ldots, x_n$ are the cell populations and is the effect of cell j on cell i and is unknown.

Aggregating across individual time courses (n=18 for GWI and n=23 for healthy controls), a single consensus network for GWI and one for healthy controls were obtained using a specialized voting scheme. These consensus networks were analyzed for differences in structure and information flow using the principles of graph theory.

Figure 3A:
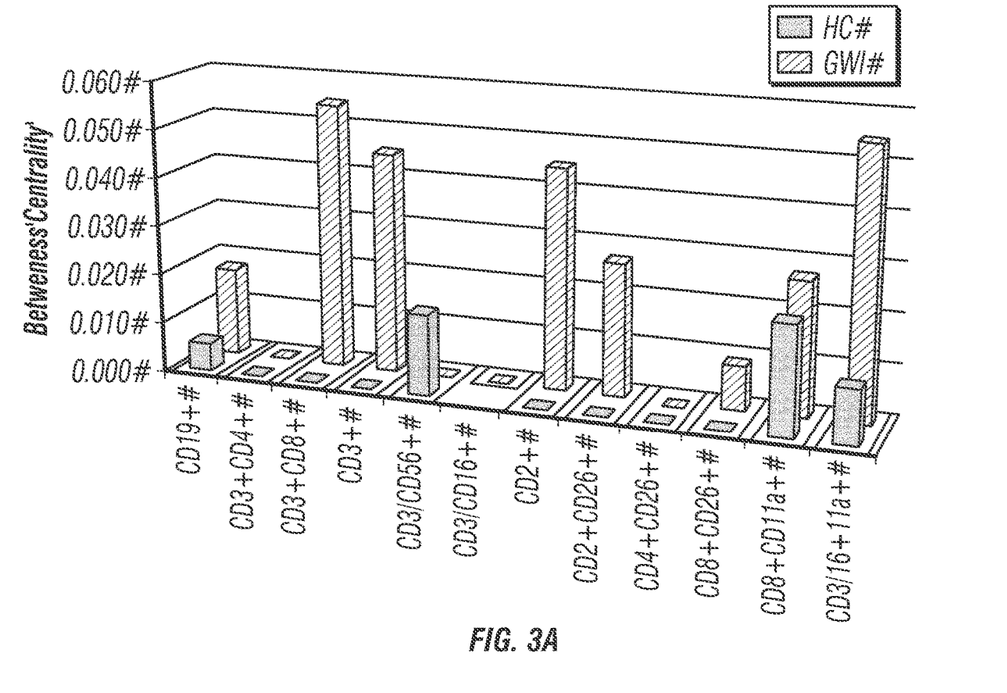
FIGS. 3A-B present data demonstrating that NK cells show a decreased role in immune information handling in Gulf War Illness (GWI).
Figure 3B:
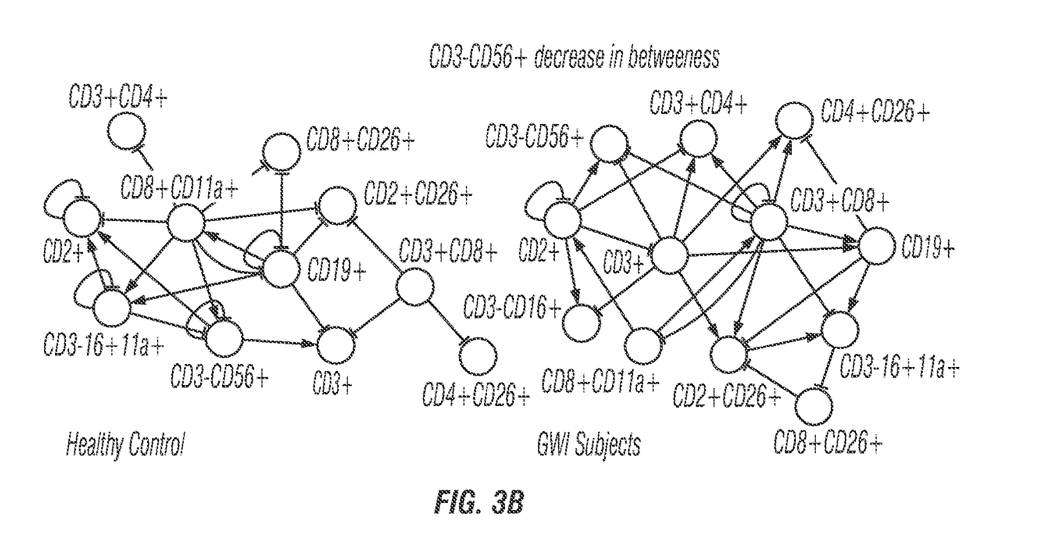
Figure 4:
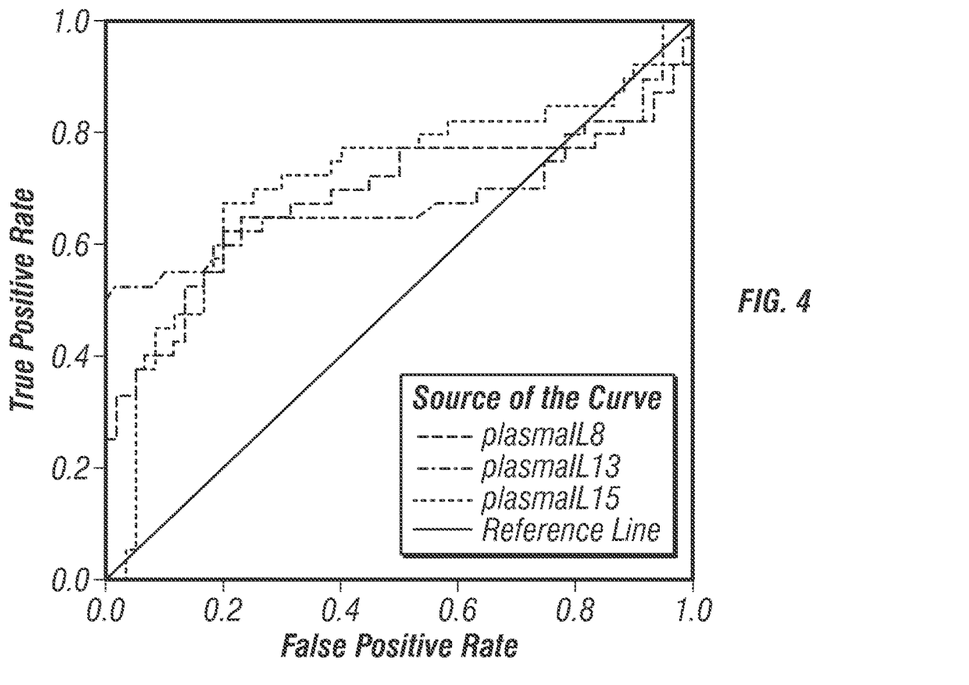
FIG. 4 is graph showing decreased biomarkers in plasma; interleukin 8 (IL-8), interleukin 13 (IL-13), and interleukin 15 (IL-15).
Figure 5:
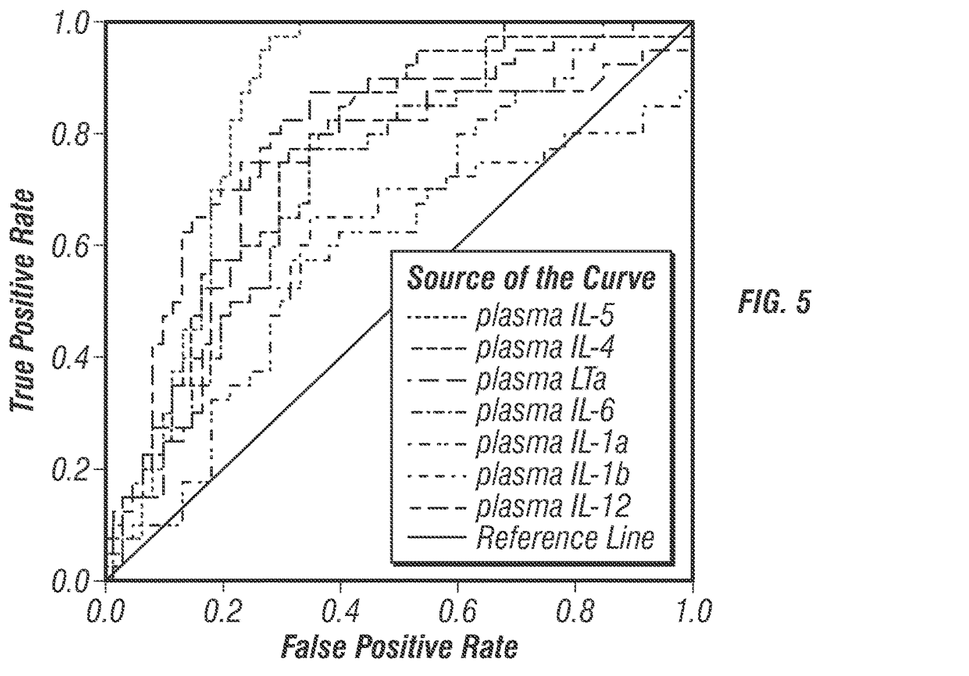
FIG. 5 is a graph showing increased biomarkers in plasma; interleukin 5 (IL-5), interleukin 4 (IL-4), lympotoxin α, interleukin 6 (IL-6), interleukin 1a (IL-1a), interleukin 1β (IL-1b), and interleukin 12 (IL-12).
Figure 6:
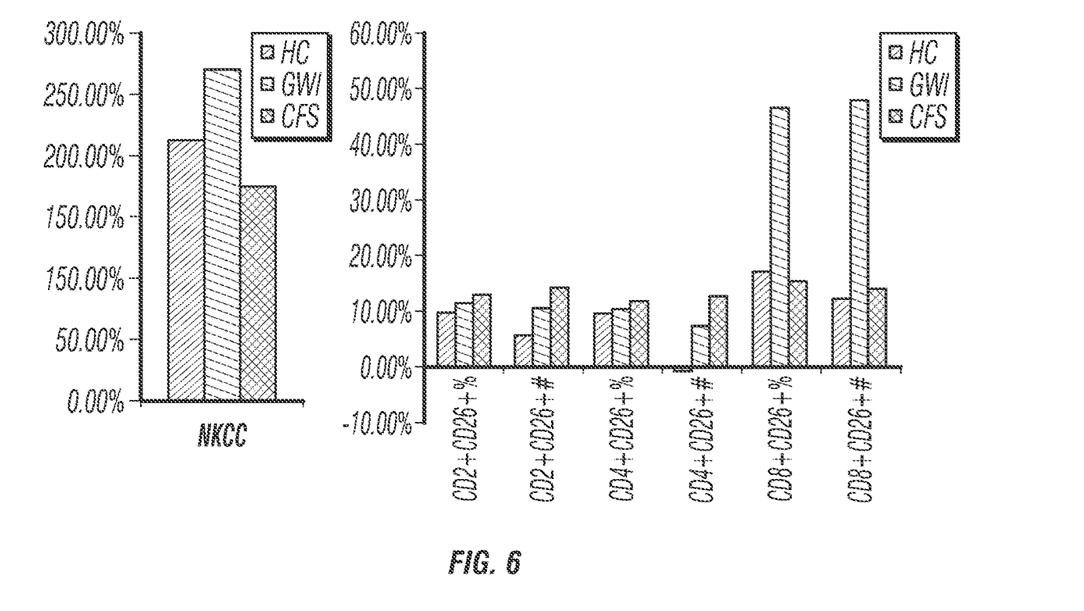
FIG. 6 is a graph showing NK (NKCC, natural killer cell cytotoxicity) flow results. In each set of three bars, healthy controls (HC) are the left bars, Gulf War Illness (GWI) are the center bars, and Chronic Fatigue Syndrome (CFS) are the right bars.
Figure 7:
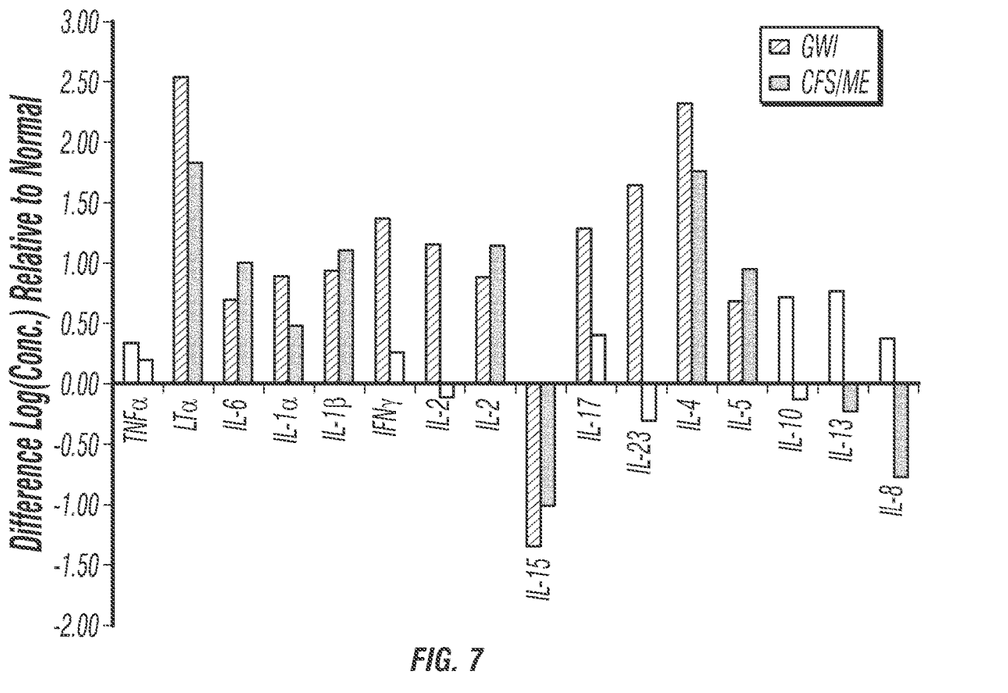
FIG. 7 is a graph showing cytokine biomarker significance; tumor necrosis factor α (TNF α), lymphtoxin α (LT α), interleukin 6 (IL-6), interleukin 1α (IL-1α), interleukin 1β (IL-1β), interferon γ (INFγ), interleukin 2 (IL-2), interleukin 12 (IL-12), interleukin 15 (IL-15), interleukin 17 (IL-17), interleukin 23 (IL-23), interleukin 4 (IL-4), interleukin 5 (IL-5), interleukin 10 (IL-10), interleukin 13 (IL-13), and interleukin 8 (IL-8). For each pair of bars, Gulf War Illness (GWI) is on the left and Myalgic Encephalomyelitis/Chronic Fatigue Syndrome (ME/CFS) is on the right.
Figure 8:
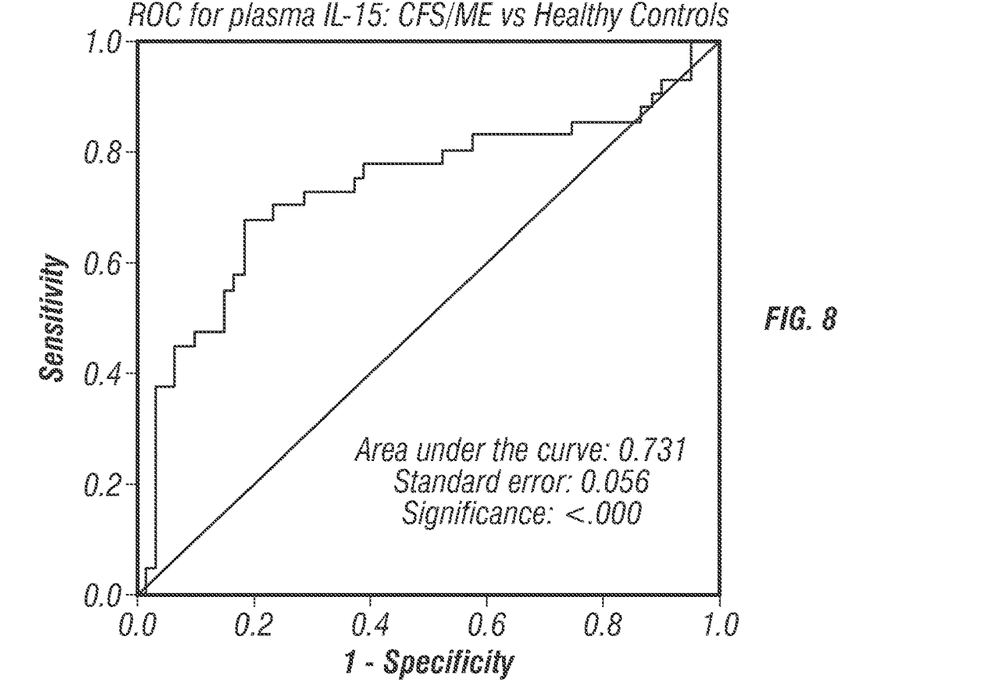
FIG. 8 is a ROC (Receiver Operating Characteristic) curve graph for plasma interleukin-15 (IL-15) ME/CFS vs. Healthy Controls. The AUC (Area Under the Curve) is 0.731; the standard error is 0.056; and the significance is <0.000.
Figure 9:
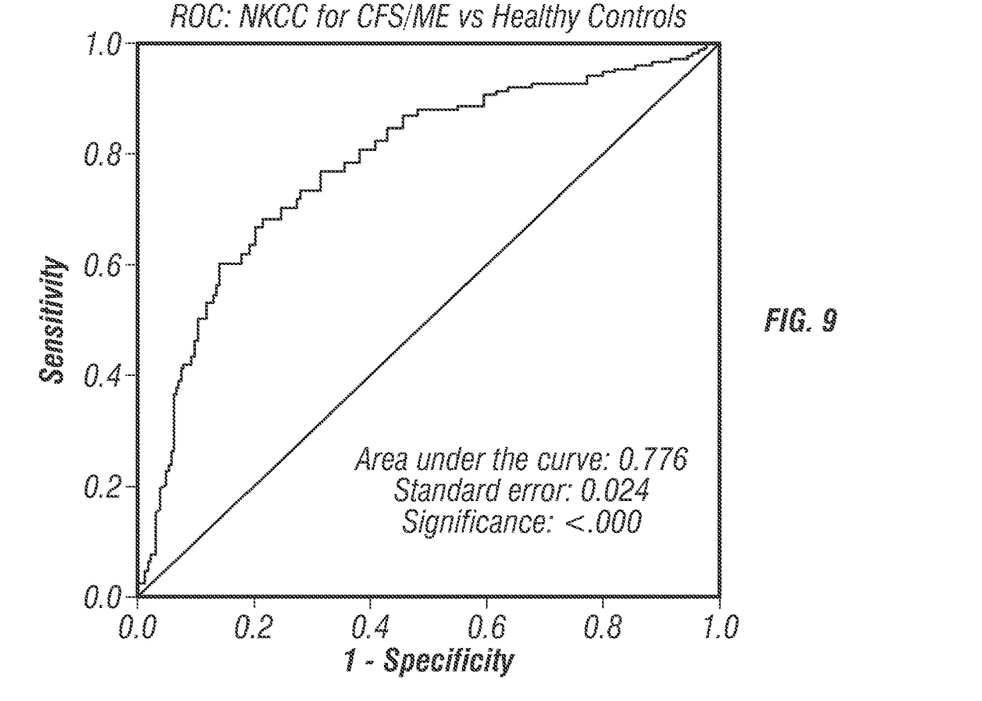
FIG. 9 is a ROC (Receiver Operating Characteristic) curve graph for the NKCC (natural killer cell cytotoxicity) for ME/CFS vs. Healthy Controls. The AUC (Area Under the Curve) is 0.776; the standard error is 0.024; and the significance is <0.000.

Analysis of the changes in the patterns of information flow showed that all immune cell subpopulations gained in information throughput in GWI compared to healthy controls, with only one exception. In GWI, the CD3−/CD56+ natural (NK) cell fraction exhibited a dramatic decrease in information throughput, based on changes in "betweeness" centrality in GWI (p=0.01), indicating this cell fraction as potential therapeutic target for treatment and development of improved treatment strategies. The results of these experiments are shown in FIGS. 3A-B.

The CD3−/CD56+ natural (NK) cell fraction was one of the most central cell populations in healthy individuals and the only cell population to lose betweeness centrality in GWI. This indicates compromised immune signal processing by this cell population. All other lymphocyte fractions increased in betweeness centrality and connectivity indicating increased immune signaling throughput in GWI. Decreased CD3−/CD56+ natural (NK) cell signaling throughput is consistent with changes in NK cell cytotoxicity reported by Fletcher M. et al. *Methods Mol Biol* 934:313-324 2012.

These results indicate immune dysregulation in GWI, particularly dysregulation of cytokines. Since the CD3−/CD56+ natural killer (NK) cell population was identified as a potential therapeutic target and interleukin 15 (IL-15) is an essential mediator of NK cells (Ranson T. et al. *Blood* 101(12); 4887-4893 2003), treatment with interleukin 15 (IL-15) was proposed as a potential therapeutic strategy in GWI. The function of interleukin-15 (IL-15) is illustrated schematically in FIG. 2.

Myalgic Encephalomyelitis/Chronic Fatigue Syndrome (ME/CFS) is a complex illness affecting approximately 1 million people in the United States alone. ME/CFS also impacts multiple systems and presents a significant clinical overlap with GWI. Both GWI and ME/CFS exhibit dysregulation of cytokines, specifically the observation of low interleukin 15 (IL-15) (Fletcher, M. et al. *Journal of Translational Medicine* 7:96, pages 1-8, 2009). Furthermore, profound impairment of NK cell function has been observed in both GWI and ME/CFS. Thus, it was proposed that stimulation with interleukin 15 (IL-15) may improve or restore NK cell function in these patients.

Figure 1:
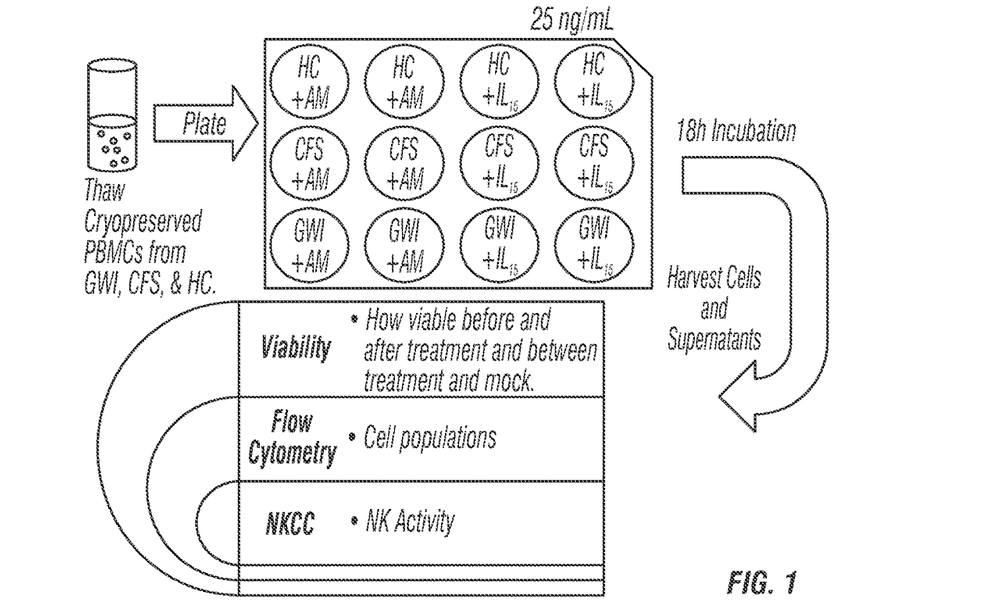
FIG. 1 is a schematic illustration of an experimental design for determining whether or not in vitro treatment with exogenous interleukin-15 (IL-15) can improve or restore Natural Killer (NK) cell function in patients having Gulf War Illness (GWI) or Myalgic Encephalomyelitis/Chronic Fatigue Syndrome (ME/CFS).

FIG. 1 is a schematic illustration of the experimental design for determining whether or not in vitro treatment with exogenous interleukin-15 (IL-15) can improve or restore Natural Killer (NK) cell function in patients having Gulf War Illness (GWI) or Myalgic Encephalomyelitis/Chronic Fatigue Syndrome (ME/CFS).

Whole blood samples collected from GWI (n=7), ME/CFS (n=9), and HC (healthy controls, n=10) subjects were recovered from cryopreservation in DMSO. Viable samples were incubated in growth medium for 18 hours with and without about 25 ng/ml of exogenous interleukin 15 (IL-15). NK cell cytotoxic function was assessed prior to cryopreservation and after stimulation using $^{51}$Cr-labeled K562 target cells and lymphocyte abundance profiled with a fluorochrome multi-parameter cytometer.

In vitro treatment with interleukin 15 (Il-15) improved NK cell function roughly 3-fold in both GWI and ME/CFS (GWI p<0.01; ME/CFS p<0.02), while CD3−/CD56+NK lymphocyte enumeration remained unchanged. Flow cytometry data exhibited significant increases in CD2+CD26+ abundance in GWI (p<0.01); no other significant cell population changes were observed. The increase of CD26+ lymphocyte expression and repair of NK cell cytotoxicity indicates that interleukin 15 (IL-15) has a positive effect on immune function in GWI and ME/CFS. The results of these experiments are shown in FIGS. 4-9.

All patents and publications mentioned in this specification are indicative of the levels of those skilled in the art to which the disclosure pertains. All patents and publications are herein incorporated by reference to the same extent as if each individual publication was specifically and individually indicated to be incorporated by reference. It is to be understood that while a certain form of the disclosure is illustrated, it is not intended to be limited to the specific form or arrangement herein described and shown. It will be apparent to those skilled in the art that various changes may be made without departing from the scope of the disclosure and the disclosure is not to be considered limited to what is shown and described in the specification. One skilled in the art will readily appreciate that the present disclosure is well adapted to carry out the objectives and obtain the ends and advantages mentioned, as well as those inherent therein. The methods, computational approaches, dynamic modeling, therapeutic targets, improved therapy strategies, consensus immune signaling networks, methods of analysis, compositions, biomarkers, procedures, and techniques described herein are presently representative of the preferred embodiments, are intended to be exemplary and are not intended as limitations on the scope. Changes therein and other uses will occur to those skilled in the art which are encompassed within the spirit of the disclosure. Although the disclosure has been described in connection with specific, preferred embodiments, it should be understood that the disclosure as ultimately claimed should not be unduly limited to such specific embodiments. Indeed various modifications of the described modes for carrying out the disclosure which are obvious to those skilled in the art are intended to be within the scope of the disclosure.

What is claimed is:

1. A method of analyzing immune signaling networks for identification of potential therapeutic targets in Myalgic Encephalomyelitis/Chronic Fatigue Syndrome (ME/CFS), the method comprising:
   selecting a group of subjects having ME/CFS as an experimental group;
   selecting a group of healthy subjects not having ME/CFS as a control group;
   subjecting both the experimental group and the control group to a graded exercise test (GXT) including an exercise challenge to induce expression of immune signaling networks in the subjects of both the experimental group and the control group in response to exercise;
   collecting blood samples from each subject tested at a predetermined number of time points, before, during, and after subjecting the subjects to the exercise challenge, wherein the time points are baseline, baseline plus 3 minutes, VO2 max (maximum effort), 10 minutes, 20 minutes, 30 minutes, 60 minutes, and 4 hours after VO2 max, and next day;
   analyzing the blood samples to identify lymphocyte cell populations and abundance in each blood sample at each of the time points;
   applying a linear rate equation model and a projection-based parameter estimation technique to the identified lymphocyte cell population at each of the time points;
   identifying coordinated dynamics of the identified lymphocyte cell populations to determine an immune signaling network, wherein the coordinated dynamics identified include information regarding direction of the immune signaling network, promotion or inhibition of the immune signaling network, and rate at which information is transmitted through the immune signaling network;
   identifying a single consensus immune signaling network for the experimental group;
   identifying a single consensus immune signaling network for the control group;
   comparing the single consensus immune signaling network for the experimental group with the single consensus immune signaling network for the control group to identify changes in structure and information flow between the networks; and
   identifying the potential therapeutic targets in ME/CFS from the changes in structure and information flow identified between the single consensus immune signaling network of the experimental group and the single consensus immune signaling network of the control group.

2. The method according to claim 1, wherein identifying coordinated dynamics further includes using complex data sets including at least one of immune function, quantification of immune peptides, quantification of neuropeptides, and genomic studies to determine patterns useful in refining biomarker panels.

3. The method according to claim 1, wherein comparing the single consensus immune signaling network for the experimental group with the single consensus immune signaling network for the control group includes applying a graph theoretical analysis.

4. The method according to claim 1, wherein identifying the potential therapeutic targets includes identifying a marker of at least one of nervous, endocrine, or immune regulation.

5. The method according to claim 4, wherein identifying a marker includes identifying a cytokine marker of immune regulation.

6. The method according to claim 5, wherein identifying a cytokine marker of immune regulation includes identifying interleukin-15 (IL-15).

7. The method according to claim 1, wherein identifying the potential therapeutic targets includes identifying a lymphocyte cell population.

8. The method according to claim 7, wherein identifying a lymphocyte cell population includes identifying a CD3−/CD56+ natural killer (NK) cell population.

9. A method of analyzing immune signaling networks for identification of potential therapeutic targets in Myalgic Encephalomyelitis/Chronic Fatigue Syndrome (ME/CFS), the method comprising:
   selecting a group of subjects having ME/CFS as an experimental group;
   selecting a group of healthy subjects not having ME/CFS as a control group;
   subjecting both the experimental group and the control group to a graded exercise test (GXT) including an exercise challenge to induce expression of immune signaling networks in the subjects of both the experimental group and the control group in response to exercise;
   collecting blood samples from each subject tested at nine time points before, during, and after subjecting the subjects to the GXT, the nine time points being baseline, baseline plus 3 minutes, VO2 max (maximum effort), 10 minutes, 20 minutes, 30 minutes, 60 minutes, and 4 hours after VO2 max, and next day;
   analyzing the blood samples to identify lymphocyte cell populations and abundance in each blood sample at each of the time points by detecting presence or absence of cluster designation (CD) surface markers;
   applying a linear rate equation model and a projection-based parameter estimation technique to the identified lymphocyte cell population at each of the time points;
   identifying coordinated dynamics of the identified lymphocyte cell populations to determine an immune signaling network, wherein the coordinated dynamics identified include information regarding direction of the immune signaling network, promotion or inhibition of the immune signaling network, and rate at which information is transmitted through the immune signaling network;
   identifying a single consensus immune signaling network for the experimental group;
   identifying a single consensus immune signaling network for the control group;

comparing the single consensus immune signaling network for the experimental group with the single consensus immune signaling network for the control group to identify changes in structure and information flow between the networks; and identifying the potential therapeutic targets in ME/CFS from the changes in structure and information flow identified between the single consensus immune signaling network of the experimental group and the single consensus immune signaling network of the control group.

10. The method according to claim 9, wherein detecting presence or absence of cluster designation (CD) surface markers includes detecting the presence or absence of CD19+, CD3+CD4+, CD3+CD8+, CD3+, CD3−/CD56+, CD3−/CD16+, CD2+, CD2+CD26+, CD4+CD26+, CD8+CD26+, CD8+CD11 a+, and CD3−/CD16+CD11 a+.

11. The method according to claim 9, wherein identifying the potential therapeutic targets includes identifying a marker of at least one of nervous, endocrine, or immune regulation.

12. The method according to claim 11, wherein identifying a marker includes identifying a cytokine marker of immune regulation.

13. The method according to claim 12, wherein identifying a cytokine marker of immune regulation includes identifying interleukin-15 (IL-15).

14. The method according to claim 9, wherein identifying the potential therapeutic targets includes identifying a lymphocyte cell population.

15. The method according to claim 14, wherein identifying a lymphocyte cell population includes identifying a CD3−/CD56+ natural killer (NK) cell population.

* * * * *